United States Patent [19]

Sergeant

[11] 4,372,310
[45] Feb. 8, 1983

[54] DIAPER WITH BLENDED YARNS

[75] Inventor: Timothy L. Sergeant, Seneca, S.C.

[73] Assignee: The Kendall Company, Boston, Mass.

[21] Appl. No.: 288,637

[22] Filed: Jul. 30, 1981

[51] Int. Cl.³ .............................................. A41B 13/02
[52] U.S. Cl. ................................................... 128/284
[58] Field of Search ............................... 128/155–156, 128/284, 287, 290 R, 290 W, 296

[56] References Cited

U.S. PATENT DOCUMENTS

| | | | |
|---|---|---|---|
| Re. 26,515 | 1/1969 | Holliday et al. | 128/284 |
| 3,109,428 | 11/1963 | Jamison | 128/284 |
| 3,367,333 | 2/1968 | Scheier | 128/284 |
| 3,409,012 | 11/1968 | Seltzer | 128/284 |
| 3,529,600 | 9/1970 | Seltzer | 128/284 |
| 3,747,601 | 7/1973 | May, Jr. | 128/284 |

Primary Examiner—C. Fred Rosenbaum
Attorney, Agent, or Firm—John F. Ryan

[57] ABSTRACT

Diapers are woven with a central panel comprising warp yarns which are a blend of hydrophobic fibers and hydrophilic fibers. Unlike yarns which are composed entirely of hydrophobic fibers, blended yarns of this type may be readily processed by conventional means through the slashing, weaving, and scouring processes. The central panel thus produced will, in use, remain dryer than panels composed entirely of hydrophilic yarns.

7 Claims, 8 Drawing Figures

DIAPER WITH BLENDED YARNS

This invention relates to a woven diaper with panel-shaped zones which vary in their moisture-absorbing capacities. More particularly it relates to such diapers wherein the absorbency differences are due to varying arrangements of spun yarns composed of absorbent fibers and spun yarns composed of blends of absorbent and non-absorbent fibers.

BACKGROUND OF THE INVENTION

It is known to weave diapers in the form of rectangular blanks, adapted to be folded to smaller rectangles for application to babies. It is also common practice to weave such diapers in a multilayered gauze-like construction, and to prefold such diapers and sew the folded blank to secure the folds in fixed position. These are termed prefolded diapers or simply prefolds.

It is also realized that wet diapers next to a baby's skin promote discomfort and even diaper rash, and attempts have been made to create diapers in which the face of the diaper to be applied next to the skin is of a hydrophobic or non-absorbent nature. Such attempts are illustrated by U.S. Pat. Nos. 3,113,570 and 3,216,421. All such previous attempts, however, have been unsuccessful due to the fact that they utilized hydrophobic yarns, such as yarns of polyamide, polyester, polyolefin and the like. Such yarns, while of lower absorbency than cotton or rayon yarns, also have a much lower shrinkage in the normal processes of purification of the woven fabric, and the subsequent multiple launderings to which the diaper is subjected. Normally, purification of a cotton diaper fabric, woven in the grey state, involves a shrinkage of between 10% and 11% in the warp direction. Since hydrophobic yarns, composed of synthetic polymers, show little or no shrinkage in such a purification process or subsequent laundering, the result is buckling and distortion of the plane of the fabric, with the development of corrugations and uneven hems, when such yarns are used in prior art diapers.

Furthermore, the elongation characteristics of hydrophobic yarns differ from the characteristics of cotton or rayon hydrophilic yarns, making them difficult to handle in the slashing and weaving process, which involves the use of a warp beam of yarns under considerable tension. Such a warp beam, composed of many hundreds of warp yarns, is conventionally fed to the loom with the yarns protected by a water-soluble size or coating removed in subsequent processing. Hydrophobic yarns are not readily wet by such coatings, necessitating special processing to assimilate them into the warp beam.

BRIEF DESCRIPTION OF THE INVENTION

It has now been found that the disadvantages of diapers comprising hydrophobic yarns and hydrophilic yarns, as set forth above, can be eliminated by the use of warp yarns which are an intimate blend of hydrophobic fibers and hydrophilic fibers, preferably in a range of 50% to 65% hydrophobic fibers and 50% to 35% hydrophilic fibers. Such yarns may be considered as semi-absorbent, and are so designated in this application, in contrast to absorbent yarns such as bleached cotton or rayon.

The present invention, therefore, relates to diapers comprising multiple layers of different absorbency characteristics. At least one layer, intended to be applied next to the infant's skin, is less moisture absorbent than other layers of the diaper due to a warp structure therein consisting substantially of semi-absorbent yarns, whereby moisture is transmitted to and retained by other layers of the diaper which have a higher absorbent capacity.

Such diaper fabrics, comprising a multiplicity of generally rectangular panels or zones, varying in absorbency characteristics and intended to be folded to form a diaper, are termed herein multipaneled diapers of zoned construction.

BRIEF DESCRIPTION OF THE DRAWINGS

The invention will be better understood by reference to the following description and drawings, in which.

DESCRIPTION OF THE INVENTION

Figure 1:
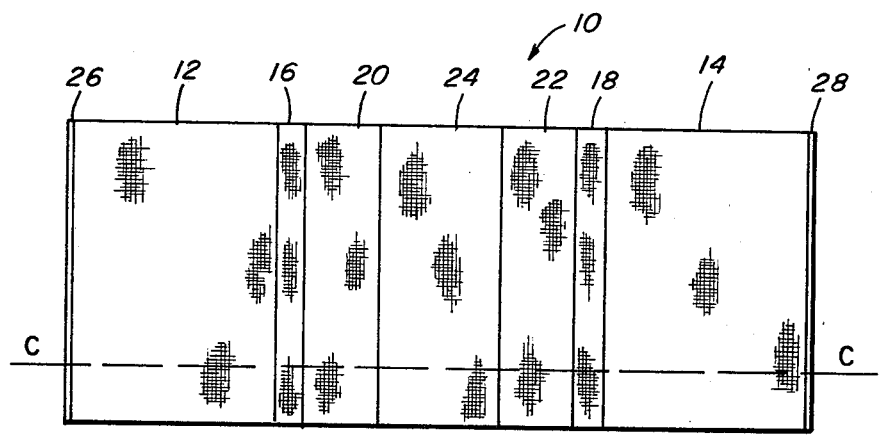
FIG. 1 is a plan view of a diaper according to one embodiment of the invention.

Referring to FIG. 1, a diaper blank is shown as consisting of a multiplicity of rectangular panels 12, 14, 20, 22, and 24, bounded on its outer edges by selvages 26 and 28, and connected internally by the wear-strips 16 and 18 which become the outer edges of the diaper after folding for use.

The central panel 24, preferably of single ply construction, consists substantially of semi-absorbent warp yarns which are a blend of hydrophobic fibers such as polyester, polyamide, polyacrylic fibers, and the like, and hydrophilic fibers such as cotton or rayon. In the finished diaper this panel is applied next to the infant's skin, where, due to its semi-absorbent nature, it tends to wick away substantial amounts of urine from the skin and transfer it to the more absorbent panels of the diaper.

Figure 2:
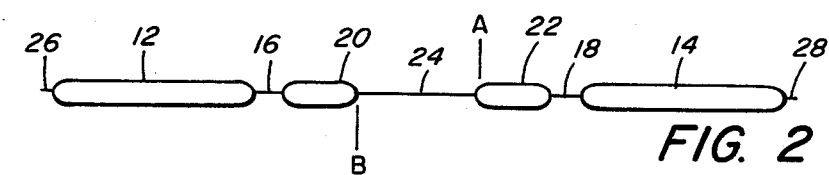
FIG. 2 is a cross-sectional view of the diaper of FIG. 1 along the line C—C.

As shown in FIG. 2, a cross-section of FIG. 1 along the line C—C, panels 12, 14, 20, and 22 are preferably of two-ply construction, for softness and ease of laundering. These four panels may be of 100% absorbent warp yarns, or may be a mixture of absorbent warp yarns and semi-absorbent warp yarns in which mixture at least 50% of the warp yarns are absorbent. It will be apparent to those skilled in the art that in order to provide diapers in which the panels possess substantially equal shrinkage tendencies in laundering, the warp yarns in panels 12, 14, 20 and 22 should not deviate in shrinkage tendency too far from the semi-absorbent warp yarns constituting the central panel 24. In ggeneral, depending on the size and twist of the yarns employed as well as the design and the tightness of the weave, satisfactory results are obtained when a central panel 24, composed of 100% semi-absorbent warp yarns, is bounded by absorbent panels 12, 14, 20, and 22 in which the warp yarns vary from 50% absorbent yarns-50% semi-absorbent yarns to 100% absorbent yarns.

Figure 8:
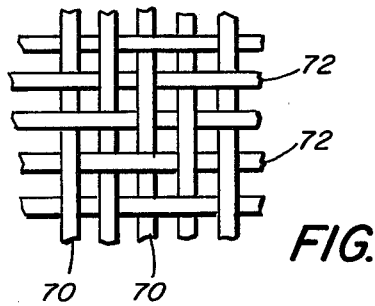
FIG. 8 is an enlarged plan view of a twill weave used in certain panels in some of the diapers of this invention.

For simplicity in weaving, it is preferable that the two-ply panels 12, 14, 20, and 22 be of square wave, although twill weave, basket weave, birdseye weave, and other weaves common in the diaper industry may be employed. The filling yarns in the diapers of this invention are preferably absorbent, throughout the body of the diaper. In the single-ply zones of the diaper, including central panel 24, wear strips 16 and 18, and selvage edges 26 and 28, a twill weave, such as FIG. 8, is preferred since such a weave adds flexibility and softness to the single-ply zones and helps to equalize warp tensions as the weave changes from single-ply to two-ply.

Figure 3:
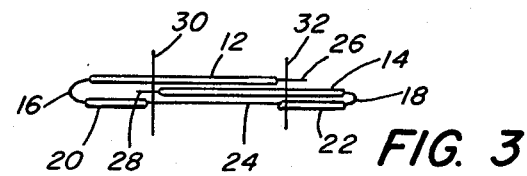
FIG. 3 is a view of the diaper of FIG. 2 folded for sewing at 30 and 32.

In forming the diaper blank of FIGS. 1 and 2 to form a prefolded, ready-to-use diaper, a folding operation is performed as shown in FIG. 3. Selvage edge 28 is brought over to point B of FIG. 2 and selvage edge 26 to point A, after which these edges are stitched along the length of the diaper fabric, as at 30 and 32 in FIGS. 3 and 21. Individual diapers of desired length are cut from the continuous fabric and secured at the cut edges by overstitching as at 34 and 36 FIG. 4, which represents a finished pefolded diaper.

SPECIFIC EMBODIMENT OF THE INVENTION

A diaper blank of zoned construction, according to FIGS. 1 and 2, was produced in a 39 inch width, using 27's cotton yarns in the filling of the fabric. At the sides of the blank, panels 12 and 14 were woven in tubular form in a square weave, with a total count of 92 warp ends and 54 picks per inch, or 46 by 27 yarns in each layer. Panels 12 and 14 were approximately 11 inches each in width, with warp yarns consisting of an equal number of randomly distributed 31's cotton yarns and 32's spun yarns of blended 50% polyester fibers and 50% cotton fibers, interwoven in a twill weave at selvages 26 and 28.

Inwardly adjacent to panels 12 and 14 the wear strips 16 and 18 were formed, each approximately 1¼ inches in width, in single layer twill weave, with 92 warp ends and 54 picks per inch, the warp yarns being a 50—50 mixture of cotton yarns and 50% polyester-50% cotton spun yarns as in panels 12 and 14.

Panels 20 and 22, adjacent to wear strips 16 and 18, were each approximately 4 inches wide and of yarn structure identical with panels 12 and 14.

Panel 24, lying between panels 20 and 22, is approximately 6½ inches wide, woven in a single layer, twill weave, with a warp consisting of 46 ends per inch, each warp yarn being a blend of 50% polyester fibers and 50% cotton fibers. The filling picks were cotton, 54 per inch.

Figure 7:
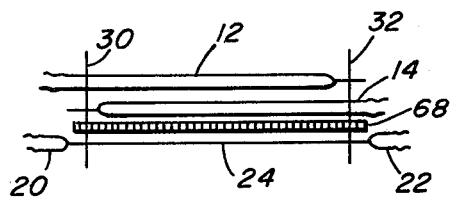
FIG. 7 is a cross-sectional view of the diaper of FIGS. 1 and 2 with an inserted absorbent layer 68.

After full-width scouring and bleaching, the fabric was plied with an absorbent insert, 68 in FIG. 7, placed on the center panel 24. This insert may be of an absorbent open-cell foam, of woven or nonwoven fibrous, or preferably, of a needle-punched fibrous batt, as of blended cotton-polyester fibers weighing 3 to 6 oz. per square yard. The assembly was folded as in FIG. 7 and stitched along the lines 30 and 32, as in FIGS. 4 and 7, thus securing the insert and the plied fabric together. After cutting the assembly to 20 inch lengths, the cut edges were secured by overedged stitching as shown at 34 and 36 in FIG. 4.

Figure 4:
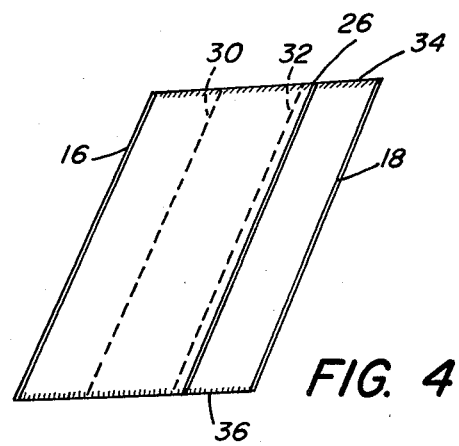
FIG. 4 is a perspective view of a finished diaper according to this invention.

The resulting prefold diaper, as shown in FIG. 4, has a lower central panel, 24 in FIGS. 2 and 3, consisting of absorbent cotton filling yarns and semi-absorbent warp yarns, consisting of a blend of cotton fibers and polyester fibers, as described above. This panel, therefore, is less absorbent than the panels constituting the rest of the diaper, and is intended to be placed next to the infant's skin. To insure proper application, the upper face of the diaper may be marked with a suitable laundry-proof index mark, or the selvage edges, 26 and 28 may incorporate a colored yarn or yarns.

When the above diaper is compared with a similar diaper composed of all absorbent cotton yarns in a moisture-distribution test, the panel 24 is noticably dryer to the touch than its all-cotton counterpart, and weight measurements show that it has retained only 40% of the moisture retained by an all-cotton panel.

OTHER EMBODIMENTS OF THE INVENTION

Figure 5:
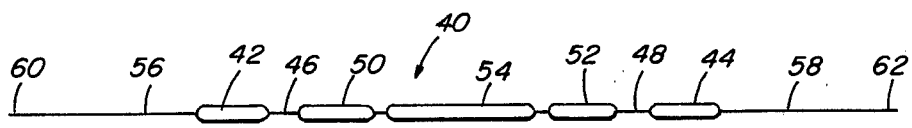
FIG. 5 is a cross-sectional view of another embodiment of a diaper according to this invention.

If it is desired to produce a diaper which has a center panel of lower absorbency on both the upper and lower surface, such a diaper is provided by constructing the diaper blank 40 in accordance with FIG. 5. The selvage edges 60 and 62 correspond in count and weave to the selvage edges 26 and 28 of the specific embodiment, above. Similarly, the two panels 56 and 58 correspond in all details to the panel 24 of FIG. 3 and the specific embodiment. The tubular panels 42, 44, 50 and 52 are of the same construction as panels 20 and 22 of the specific embodiment, and the wear strips 46 and 48 duplicate the wear strips 16 and 18 of the specific embodiment.

The tubular center panel may be of a construction identical with the absorbent panels 12 and 14 of the specific embodiment, or they may comprise heavier cotton yarns, such as 20's or heavier, for added absorbency. Such heavier yarns may require a lower twist multiple than the 31's used throughout the warp in the rest of the diaper, in order to match the shrinkage characteristics of the other panels. However, a lower twist multiple will not decrease the abrasion characteristic of the diaper since this panel 54 is protected by the layers 56 and 58 in the end product.

Figure 6:
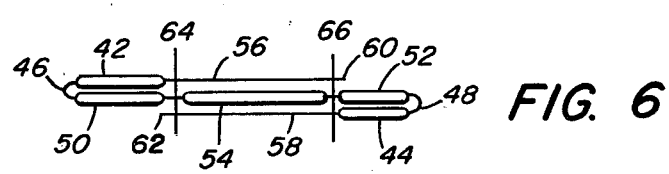
FIG. 6 is a view of the diaper of FIG. 5 folded for sewing at 64 and 66.

The diaper blank of FIG. 5, after purification is folded as shown in FIG. 6 and stitched at 64 and 66 to form a prefold diaper with central semi-absorbent panels on each face and a more absorbent panel between those faces.

What is claimed is:

1. A multi-paneled diaper of zoned construction, said diaper containing at least one panel comprising absorbent filling yarns and warp yarns consisting of a blend of hydrophobic fibers and hydrophilic fibers.

2. The diaper according to claim 1 in which the hydrophobic fibers in the warp yarns of said one panel are polyester fibers and the hydrophilic fibers blended with said hydrophobic fibers are cotton fibers.

3. The diaper according to claim 1 in which the warp yarns in said one panel are a blend of 50% polyester fibers and 50% cotton fibers, and the absorbent filling yarns are composed of cotton fibers.

4. The diaper according to claim 1 in which said one panel comprising absorbent filling yarns and warp yarns consisting of a blend of hydrophobic fibers and hydrophilic fibers is disposed substantially centrally of said diaper.

5. The diaper according to claim 4 wherein said one panel is bounded along both longitudinal edges by panels comprising warp yarns of absorbent fibers.

6. The diaper according to claim 5 wherein the panels bounding said one panel comprise a mixture of cotton warp yarns and yarns of 50% cotton fibers and 50% polyester fibers.

7. The diaper according to claim 6 wherein the panels bounding said one panel consist of 50% cotton warp yarns and 50% warp yarns composed of 50% cotton fibers and 50% polyester fibers.

* * * * *